US005645821A

United States Patent [19]
Libin

[11] Patent Number: 5,645,821
[45] Date of Patent: Jul. 8, 1997

[54] ALKALINE ORAL HYGIENE COMPOSITION

[76] Inventor: Barry M. Libin, 15 Thornhedge Rd., Bellport, N.Y. 11713

[21] Appl. No.: 540,249

[22] Filed: Oct. 6, 1995

[51] Int. Cl.$^6$ .................................................. A61K 7/16
[52] U.S. Cl. .................................................. 424/49
[58] Field of Search ........................................ 424/49–58

[56] References Cited

U.S. PATENT DOCUMENTS

| | | | |
|---|---|---|---|
| 1,536,305 | 5/1925 | Nitardy, I | 424/49 |
| 1,622,391 | 3/1927 | Nitardy, II et al. | 424/49 |
| 1,691,504 | 11/1928 | Vogt | 424/49 |
| 2,069,157 | 1/1937 | Sahyun | 424/49 |
| 4,098,435 | 7/1978 | Weyn | 222/94 |
| 4,690,776 | 9/1987 | Smigel | 424/49 |
| 4,770,324 | 9/1988 | Parnell et al. | 424/49 |
| 4,795,630 | 1/1989 | Okovchi et al. | 424/49 |
| 4,871,396 | 10/1989 | Tsujita et al. | 424/49 |
| 4,976,955 | 12/1990 | Libin, I | 424/53 |
| 4,983,379 | 1/1991 | Schaeffer | 424/52 |
| 5,000,942 | 3/1991 | Libin, II | 424/53 |
| 5,039,515 | 8/1991 | Korf | 424/53 |

*Primary Examiner*—Shep K. Rose
*Attorney, Agent, or Firm*—Michael Ebert

[57] ABSTRACT

An alkaline oral hygiene composition which when brushed or otherwise applied to surfaces of the teeth and adjacent gingival tissue functions not only to clean and whiten the teeth but also to prevent the formation of plaque, to neutralize acids causing tooth decay and to remove from the surfaces extraneous material which discolor the teeth. Included in the composition is at least one alkaline metal compound powder having minimal abrasivity which imparts to the composition an overall pH in excess of 9 whereby when used in the acidic environment of the oral cavity, retains its alkalinity to counteract the activity of pathogenic bacteria causing plaque and to neutralize the production in the oral cavity of acids causing tooth decay. The alkaline composition also saponifies foreign material attached to the teeth surfaces so that these materials which discolor the teeth can be washed away.

10 Claims, No Drawings

ALKALINE ORAL HYGIENE COMPOSITION

BACKGROUND OF INVENTION

1. Field of Invention

This invention relates generally to oral hygiene compositions which are brushed or otherwise applied to surfaces of the teeth and adjacent gum tissues, and in particular to a composition which includes an alkaline metal compound powder, the composition not only acting to clean and whiten the teeth but also to counteract the formation of plaque, to neutralize acids responsible for tooth decay, and to remove extraneous material from the surfaces of the teeth which otherwise discolor the teeth.

2. Status of Prior Art

As noted in the Leopold U.S. Pat. No. 4,485,089, the typical toothpaste for cleaning and whitening teeth makes use for this purpose of a dental abrasive, such as silica. Such abrasives score and damage the enamel surface of the teeth. Also included in a typical toothpaste is a cleaning agent such as dicalcium phosphate, water and a humectant, such as glycerin or sorbitol. A humectant serves to retain moisture in the toothpaste, particularly, at the nozzle of the tube where the paste can be in prolonged contact with the air.

A conventional toothpaste mainly carries out a cosmetic function. While it serves in conjunction with a toothbrush to clean the teeth and improve their appearance, the toothpaste does little to prevent tooth decay, to inhibit the growth of plaque or to in other respects maintain the teeth and gums in a healthy condition.

As noted in the Libin U.S. Pat. No. 5,000,949, dental plaque is constituted by a thin layer of mucuaginous film which is subject to invasion by colonizing bacteria. Metabolic activity of these bacteria in the presence of dietary carbohydrates leads to the production of acetic and other acids. These acids attack soft gum tissue, thereby causing gingivitis; that is, the redening and swelling of the normally pink gums, often accompanied by bleeding. These acids also react with the calcium of the teeth and the resultant decalcification of the organic matrix or dentin is such as to allow for the further invasion of bacteria and liquefying enzymes. Hence vital to sound oral hygiene is the reduction and control of dental plaque.

The Libin '949 patent provides an oral hygiene composition that includes a blend of magnesium peroxide and calcium peroxide compounds which together release active oxygen functioning as an oxidizing germicidal agent to destroy anerobic bacteria associated with dental plaque and periodontal diseases.

Toothpaste compositions of the type heretofore known make use of relatively coarse abrasive agents, such as silica. While these serve to whiten teeth, with repeated use, they wear away the superficial surface of the tooth enamel. Because this enamel does not regenerate, the teeth become subject to attack and decay. Moreover, most toothpastes are somewhat acidic in nature, and the combination of acidity and abrasiveness will in time destroy porcelain and other bonding agents which simulate natural enamel and are now commonly applied to teeth surfaces to afford a more attractive veneer.

It is desirable, therefore, that a toothpaste in cleaning and whitening teeth, not do so at the expense of the natural enamel or the bonding agent which simulates the natural enamel.

And it is also desirable that the toothpaste promote the health of the dental regions in the oral cavity.

SUMMARY OF INVENTION

In view of the foregoing, the main object of this invention is to provide an oral hygiene composition having minimal abrasivity which when brushed or otherwise applied to the surfaces of the teeth and adjacent gingival tissue, functions not only to clean and whiten the teeth without damaging the enamel, but also to counteract the formation of plaque, to prevent dental decay and to remove from the surfaces of the teeth extraneous material which otherwise discolor the teeth.

More specifically, an object of the invention is to provide a composition of the above type which includes an alkaline metal compound powder that imparts a high overall degree of alkalinity to the composition, whereby when applied in the acidic environment of the oral cavity and saliva, the composition retains its alkalinity and effectiveness.

Also an object of the invention is to provide a toothpaste of the above type having the consistency of a paste or cream.

Yet another object of the invention is to provide a composition of the above type which remains stable in a toothpaste tube or other dispenser.

Briefly stated, these objects are attained in an oral hygiene composition containing deionized water in an amount sufficient to confer wetness to the composition, a humectant, such as sorbitol, to retain moisture, an anionic surfactant, such as sodium lauryl sulfate having detergent and foaming properties, and a gelling agent, such as glycerin.

Also included in the composition to impart alkalinity thereto as well as a minimal degree of abrasivity is at least one alkaline metal compound powder, such as magnesium hydroxide.

The overall pH of the composition exceeds 9 whereby when the composition is used in the acidic environment of the oral cavity and the saliva therein, the composition then retains its alkalinity to counteract the formation of plaque and to penetrate and saponify extraneous materials adhering to the surfaces of the teeth and on the adjacent gum tissues, the saponified material being released from these surfaces and being washed away.

DETAILED DESCRIPTION OF INVENTION

An oral hygiene composition in accordance with the invention includes at least one alkaline metal compound powder which imparts an overall alkalinity to the composition exceeding pH 9 whereby when brushed on or otherwise applied to the surfaces of the teeth and the adjacent gingival tissues, the composition retains its alkalinity despite the acidic environment of the oral cavity and the saliva contained therein.

The alkalinity of the composition gives rise to activities in the regions in which the composition is applied. These activities has the following beneficial effects which together promote the health of the teeth and adjacent gingival tissues treated by the composition.

Effect I.

The applied alkaline composition interferes with the normal life cycles of pathogenic bacteria present in the oral cavity and prevents proliferation thereof. It is only when these bacteria. such as porphyromonas gingivalis is allowed to proliferate that periodontal diseases occur. Alkalinity discourages excessive growth and colonization of these bacteria.

Effect II.

The applied alkaline composition neutralizes the production of acids produced by streptococcus mutans, salvaris and other bacterial species found in the oral cavity and implicated in causing dental decay. Such acids result from the normal metabolism of the bacteria, usually upon a carbohydrate substrate. The acids act to decalcify the matrix of the enamel surface and thereby produce dental decay.

Effect III.

The alkaline composition burns through or penetrates and saponifies the extraneous material forming on and discoloring the enamel surfaces of the teeth. These foreign materials usually occur initially by reason of the formation of a protein matrix or pellicle which attaches itself to the tooth enamel and stains the enamel. The discoloration of the enamel makes it to appear to be darker or to have a yellowish tinge that deviates from the normal white appearance of healthy teeth.

These stains can be removed and the discoloration erased to return the tooth to its original whiter and lustrous appearance if the protein pellicle can effectively be "burned" away, or if the enamel surface can be thoroughly interfaced with an alkaline soapy material that will surround the protein pellicle and other foreign matter extraneous to the tooth enamel, and then allow it to be rinsed away.

The effectiveness of soap depends on the action of an alkali on fats by the process of saponification. Soap lowers the surface tension of water and thereby permits emulsification of fat-bearing soil particles so that they can be washed away from the soiled surface. The detergent action of an alkaline soap is caused by the long hydrocarbon chains in their molecules. These chains are oil-soluble and have at one end the carboxylic acid group which is water soluble. This enables an alkali powder and water to emulsify the oil particles contained in the extraneous material attached to the enamel of teeth and to float them away from the enamel.

The alkalinity of the composition, because it exceeds pH 9 and remains alkaline in the acidic environment of the oral cavity, potentiates the surface activity of the material, thereby reducing surface tension and increasing the liquid's spreading and wetting properties. The surface-active molecules concentrate at the interfaces between water and the oily foreign particles adhering to the enamel surface of the teeth. One end of the molecule seeks the water and the other the oily foreign substances. At these interfaces, the surface-active agent emulsify and intermix with the toothpaste-salivary mixture in the mouth. Following the attachment of the hydrophobic part to the solid foreign substances, it is broken up into small beads that can be washed away through the mechanical actions of tooth brushing. By rinsing, the surface-active molecules pull the foreign substances away from the enamel into the water.

The following is a listing of the preferred ingredients for an alkaline oral hygiene composition in accordance with the invention. The composition preferably is in a viscous paste or cream form so that it may be brushed or otherwise applied to the surface of the teeth and the adjacent gingival tissues and retained thereon for a period sufficient to permit the above-identified effects to take place.

Ingredients by Weight

A. Magnesium hydroxide—from 0.5 to 10% (This alkaline metal compound is in the form of a fine white powder, almost insoluble in water. This ingredient serves to adjust the pH of the composition so that its overall pH is in excess of 9.)

B. Magnesium carbonate—from 0.5 to 20% (This alkaline metal compound, in the form of a fine white powder, almost insoluble in water, is mainly responsible for the overall pH of the composition and also serves as a cleansing agent of minimal abrasivity.)

C. Sodium carboxyl methyl cellulose (CMC)—from 0.5 to 10% (This ingredient serves as a thickening agent.)

D. Glycerin—from 5% to 20% (This ingredient acts as a gelling agent.)

E. De-ionized water—from 0.5 to 40% (This water is an amount which confers suitable wetness to the cream or paste in accordance with its desired viscosity.)

F. Dicalcium phosphate—from 0.5 to 10% (Cleansing agent.)

G. Sorbital—from 10% to 70% This ingredient acts as a humectant to retain moisture in the composition and also gives body to the paste.)

H. Sodium lauryl sulfate—from 0.5 to 10% (An anionic surfactant having detergent and foaming properties.)

I. Pepermint Oil—from 0.1 to 5% (Flavoring agent.)

In preparing this composition, first the CMC is dispersed in the glycerin, after which water and sorbitol are added, these ingredients being intermingled to produce a gel. Then the other ingredients are stirred into the gel to complete the composition.

The relative amounts of the magnesium hydroxide and magnesium carbonate are such that the overall pH of the composition exceeds 9. Also useable as an alkaline metal compound is calcium carbonate, a white powder which occurs in nature as chalk and has minimal abrasivity. The pepermint oil is but one of many useable flavoring agents and in practice other flavoring sweetening agents may be used to impart any desired taste or flavor to the composition.

The following is a preferred example of an alkaline oral hygiene composition in accordance with the invention. The ingredients being numbered from 1 to 11 and the phases in which the ingredients are intermixed being identified as phases A, B, and C.

EXAMPLE

| NO. | PHASE | INGREDIENT | % BY WEIGHT |
|---|---|---|---|
| 1 | A | GLYCERIN 96% | 10.00 |
| 2 | A | CMC-9M31XF | 2.00 |
| 3 | A | SORBITOL 70% | 35.00 |
| 4 | A | DEIONIZED WATER | 23.40 |
| 5 | B | CALCIUM CARBONATE ppt. l.t. | 16.10 |
| 6 | B | MAGNESIUM CARBONATE | 2.00 |
| 7 | B | MAGNESIUM HYDROXIDE | 4.40 |
| 8 | C | SORBITOL, 70% | 5.00 |
| 9 | C | SODIUM LAURYL SULFATE | 1.00 |
| 10 | C | SODIUM SACCHARINE | 0.10 |
| 11 | C | FLAVOR MF-4939/2 | 1.00 |

In manufacturing this composition, in phase A dispersed in the glycerin is CMC to which sorbitol and the water are then added, these ingredients being intermixed to produce a gel. In phase B, calcium carbonate, magnesium carbonate and magnesium hydroxide are added to and intermingled with the gel to produce a batch. And in phase C, added to and intermingled with this batch are sorbitol, sodium lauryl sulfate, sodium saccharine and flavor to complete the composition.

While there has been shown a preferred embodiment of an alkaline oral hygiene composition in accordance with the invention, it will be appreciated that many changes and modifications may be made therein, without however departing from the essential spirit thereof. Thus instead of calcium carbonate one may use in the composition as an alkaline metal compound, zinc carbonate or other innocuous alkaline metal compounds in a fine powder form having minimal abrasiveness so that the powder acts to polish, not sand the teeth enamel.

And one may add to the composition fluorides of the types found in many commercially available tooth pastes, for fluorides do not react with the other ingredients and produce beneficial results.

The present invention does not rely on abrasivity to clean and whiten the enamel surface of the teeth, but on the friction of toothbrush bristles in combination with the saponification and the soap-like action produced by the alkaline metal compound powders.

I claim:

1. A peroxide-free alkaline oral hygiene composition in a paste or cream form applicable to surfaces of teeth and adjacent gingival tissues in an acidic environment of the oral cavity, said composition consisting essentially of:

A. water in an amount sufficient to impart wetness to the composition;

B. a gelling agent to form said paste or cream;

C. an anionic surfactant in an amount sufficient to impart detergent and foaming properties to the composition; and D. a mixture of magnesium hydroxide, magnesium carbonate and calcium carbonate in fine powder form serving as cleansing agents having minimum abrasiveness in relative amounts sufficient to impart to the composition an overall pH in excess of about 9 to cause said composition to retain its alkalinity in said acidic environment and thereby counteract the formation of plaque and neutralize acids in the oral cavity environment causing tooth decay, the alkaline composition acting to saponify foreign materials accumulating on the surfaces of the teeth and adjacent gingival tissues whereby those materials may be washed away.

2. A composition as set forth in claim 1, in which said water is deionized, and further including a humectant to retain moisture in the composition.

3. A composition as set forth in claim 2, in which the humectant is sorbitol.

4. A composition as set forth in claim 1, further including a thickening agent.

5. A composition as set forth in claim 4, in which the thickening agent is sodium carboxyl methyl cellulose.

6. A composition as set forth in claim 1, in which the surfactant is sodium lauryl sulfate.

7. A composition as set forth in claim 1, in which the gelling agent is glycerin.

8. A composition as set forth in claim 1, in which the relative amount of magnesium hydroxide by weight is from 0.5 to 10 percent.

9. A composition as set forth in claim 1, in which to the relative amount of magnesium carbonate by weight is from 0.5 to 20 percent.

10. A composition as set forth in claim 1, in which the relative amounts by weight is about 4 percent magnesium hydroxide, about 2 percent magnesium carbonate and about 16 percent calcium carbonate.

* * * * *